US006307066B1

(12) United States Patent
Murthy et al.

(10) Patent No.: US 6,307,066 B1
(45) Date of Patent: *Oct. 23, 2001

(54) PROCESS FOR PRODUCING SIMVASTATIN

(75) Inventors: K. S. Keshava Murthy, Brantford; Stephen E. Horne, Burlington; Gamini Weeratunga; Shawn Young, both of Brantford, all of (CA)

(73) Assignee: Brantford Chemicals Inc., Brantford (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/754,677

(22) Filed: Nov. 21, 1996

(30) Foreign Application Priority Data

Sep. 19, 1996 (CA) .................................... 2185961

(51) Int. Cl.[7] .................................................. C07D 309/30
(52) U.S. Cl. ............................................. 549/292; 549/214
(58) Field of Search ..................................... 549/292, 214

(56) References Cited

U.S. PATENT DOCUMENTS

| 4,444,784 | 4/1984 | Hoffman et al. | 424/279 |
| 4,582,915 | 4/1986 | Sleteinger et al. | 549/292 |
| 4,820,850 | 4/1989 | Verhoeven et al. | 549/292 |
| 5,159,104 | 10/1992 | Dabora et al. | 560/119 |
| 5,393,893 | 2/1995 | Kubela et al. | 549/292 |

FOREIGN PATENT DOCUMENTS

| 1199322 | 1/1986 | (CA) . |
| 1287063 | 7/1991 | (CA) . |
| 2067722 | 11/1992 | (CA) . |

OTHER PUBLICATIONS

Askin D., Verhoeven T.R., Liu T.M.H., and Shinkai, I., Synthesis of Synvinolin: Extremely High Conversion Alkylation of an Ester Enolate *J. Org. Chem 1991*, 56, 4929.

Wiberg K.B., Laidig, K.E., Acidity of (Z)– an (E)–Methyl Acetates: Relationship to Meldrum's Acid *J. Am. Chem. Soc. 1998*, 110, 1872.

Beak P., Meyers A.I. Stereo– and Regiocontrol by Complex Induced Proximity Effects: Reactions of Organolithium Compounds *Acc. Chem. Res. 1986*, 19, 356.

Ferrier R.J., Carbohydrate Boronates *Advances in Carbohydrate Chemistry and Biochemistry*, 1978, 35, 31–80.

*Primary Examiner*—Amelia Owens
(74) *Attorney, Agent, or Firm*—Ivor M. Hughes; Neil H. Hughes; Marcelo K. Sarkis

(57) ABSTRACT

A process for manufacturing Simvastatin is provided comprising reacting lovastatin with an organic boronic acid to produce a derivative of lovastatin (lovastatin phenylboronate) methylating the 2-methylbutyryloxy group on the lovastatin derivative to form a 2,2-dimethylbutyryloxy group on the lovastatin derivative and thereafter removing the boronate group to produce simvastatin.

45 Claims, No Drawings

PROCESS FOR PRODUCING SIMVASTATIN

FIELD OF INVENTION

This invention relates to the preparation of SIMVASTATIN. This invention also relates to the purification of intermediates which may be used in the preparation of simvastatin. More broadly, this invention relates to processes for the alkylation at an α-carbon of an ester (containing one or two α-hydrogens) in a molecule which also contains a β-hydroxylactone functional group with one or two α-hydrogens.

BACKGROUND OF THE INVENTION

Mevastatin (also known as compactin) and lovastatin (also known as mevinolin) are naturally occurring HMG-CoA reductase inhibitors. These compounds have been used medicinally in the control of human serum cholesterol levels. Both compounds contain a (2S)-2-methylbutyryloxy substituent at the C-8 position of their hexahydronaphthalene nucleus and both produce medicinal analogues with increased potency towards HMG-CoA reductase when the aforementioned 2-methylbutyryloxy side chain is converted into a 2,2-dimethylbutyryloxy group. The analogue which is obtained from lovastatin by such a conversion is known as simvastatin. A method for the commercial scale production of simvastatin from lovastatin is the subject of the present invention.

DISCUSSION OF PRIOR ART

Several processes for the preparation of simvastatin from lovastatin are reported. Two of these methods involve a deacylation/reacylation procedure. The prior art discussed in U.S. Pat. No. 4,444,784 (84)/CA1,199,322 (86, Merck) teaches the conversion of lovastatin to several 8-acyloxy derivatives, including simvastatin.

Lovastatin is completely hydrolyzed to remove the 2-methylbutyryl side chain and to simultaneously open its 6-membered lactone ring to produce a trihydroxy acid. The trihydroxy acid compound is then heated in order to effect relactonization and a dihydroxylactone is obtained. The free hydroxy group in the lactone ring of the dihydroxylactone is protected as a tert-butyldimethylsilyl ether and then the hydroxy group at C-8 of the hexahydronaphthalene ring system is esterified using 2,2-dimethylbutyryl chloride. The t-butyldimethylsilyl protecting group is then removed in the final step using tetrabutylammonium fluoride to produce simvastatin.

Flowsheet for US 4,444,784 (84)/CA 1,199,322 (86)

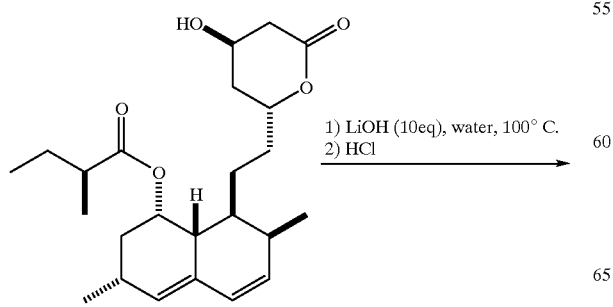

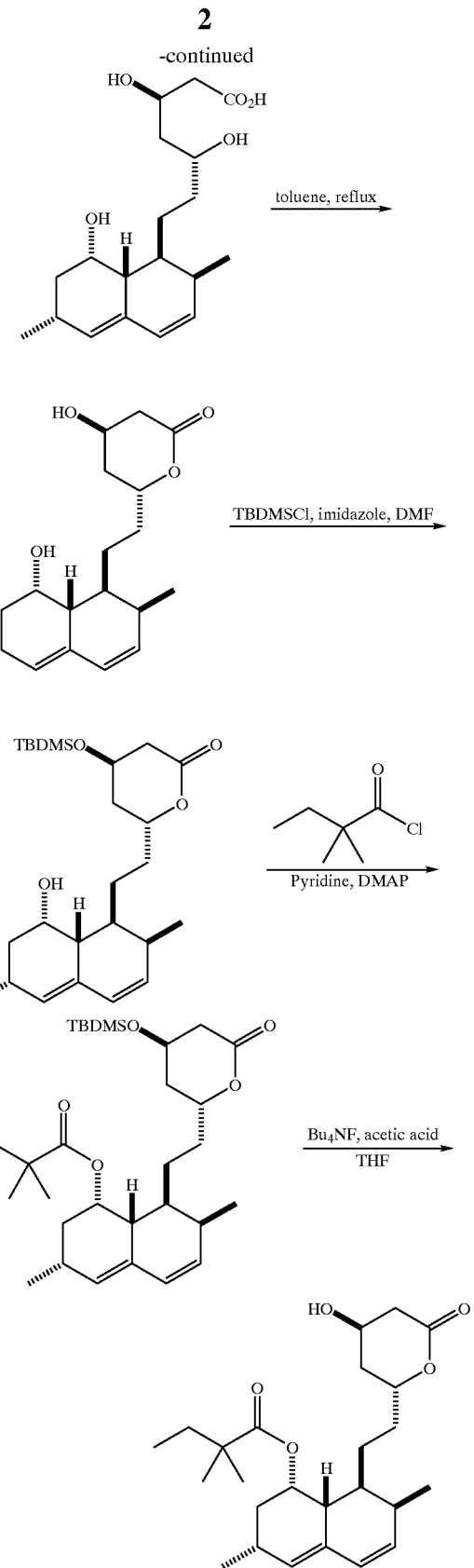

In U.S. Pat. No. 5,159,104 (92)/CA 2,067,722 (Merck), a deacylation/reacylation approach is also used but an acyl protecting group is used instead of a tert-butyldimethylsilyl group. The dihydroxylactone (obtained as discussed above from lovastatin) is acetylated at the more reactive lactone hydroxy group using acetic anhydride. The acetate which is obtained is then reacted with 2,2-dimethylbutyryl chloride to produce the acetate of simvastatin. The acetate group is then removed by either of two methods. In the first procedure, the acetate of simvastatin is reacted with methanol under acidic conditions to produce a dihydroxy methyl ester. This methyl ester is then reacted with ammonium hydroxide to produce a dihydroxy ammonium salt. The ammonium salt is heated in order to cause relactonization and simvastatin is obtained.

strategy in which lovastatin is transformed into a protected intermediate wherein the lactone moiety of lovastatin has been intentionally opened. This strategy is undertaken in order to intentionally alter the acidity of the hydrogen atoms which are located at the α-position of the lactone group of lovastatin. The ring opening and protection of the lactone group then allows treatment with a suitable base and hence the removal of the α-proton in the 2-methylbutyryloxy side chain. The enolate species which results is then methylated to produce a 2,2-dimethylbutyryloxy side chain. Protecting groups are then removed, and a thermal reaction is then employed to effect lactonization to produce simvastatin. These three technologies are examined in more detail below.

Flowsheet for US 5,159,104 (92)/CA 2,067,722 (92)

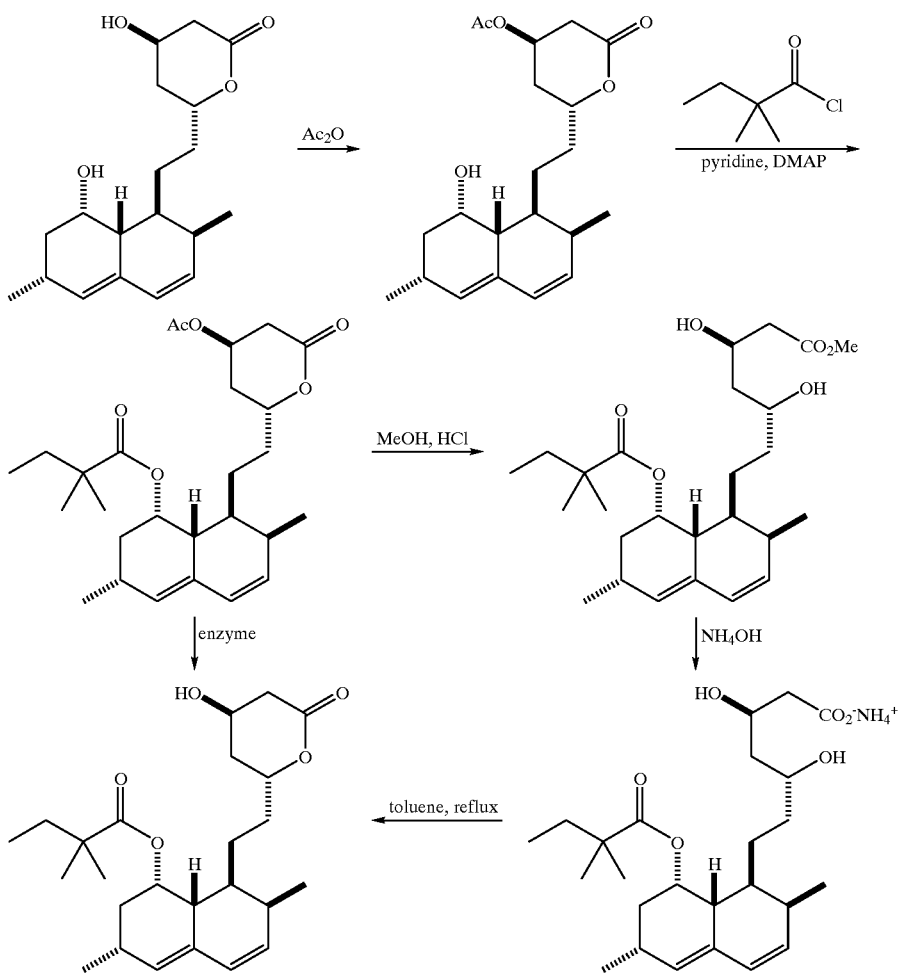

In the second procedure, the acetate of simvastatin is hydrolyzed using an enzymatic preparation.

Previously, it has been reported that lovastatin (in its lactone form) cannot be converted directly to simvastatin by an enolate alkylation reaction because of concurrent alkylation at the lactone α-position (D. Askin, T. R. Verhoeven, H. Liu, and I. Shinkai *J. Org. Chem.* 1991, 56, 4929) due to the higher acidity (approximately 3 pKa units) of the lactone α-hydrogens compared with the side chain ester α-hydrogen (K. B. Wiberg, K. E. Laidig *J. Am. Chem. Soc.* 1988, 110, 1872). The technologies discussed in U.S. Pat. No. 4,582,915 (86), U.S. Pat. No. 4,820,850 (89)/CA 1,287,063 (91), and U.S. Pat. No. 5,393,893 (95) therefore share a common In the process described in U.S. Pat. No. 4,582,915 (86, Merck), lovastatin is reacted with potassium hydroxide and is converted into a potassium salt of a dihydroxy acid compound. The potassium salt is then enolized using lithium pyrrolidide and the enolate intermediate is alkylated with methyl iodide to produce a dihydroxy acid compound with the 2,2-dimethylated side chain.

The dihydroxy acid is then heated and water is azeotropically removed to produce simvastatin.

Flowsheet for US 4,582,915 (86)

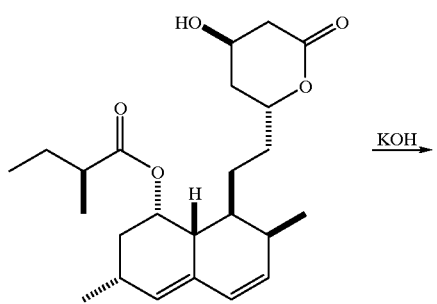

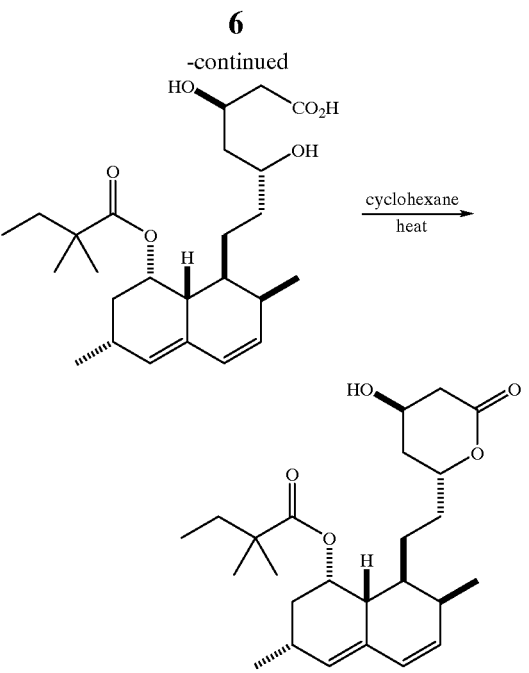

In U.S. Pat. No. 5,393,893 (95, Apotex), lovastatin is reacted with cyclohexylamine to open the lactone ring and to produce a lovastatin dihydroxycyclohexylamide. The dihydroxy unit is protected by reacting the intermediate with phenylboronic acid to produce a lovastatin cyclohexylamide boronate. The boronate is alkylated using lithium pyrrolidide and methyl iodide and with an aqueous workup simvastatin cyclohexylamide boronate is produced. The boronate group is removed by hydrolysis with sodium hydroxide to produce a simvastatin cyclohexylamide. The amide group is removed and the lactone ring is reformed by heating with acetic acid.

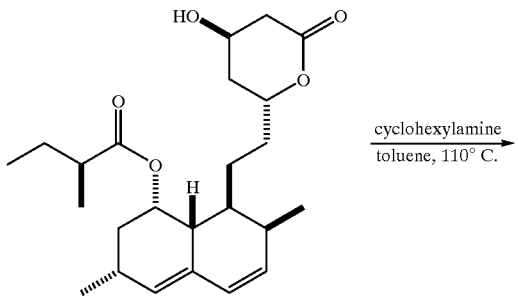

Flowsheet for US 5,393,893 (95)

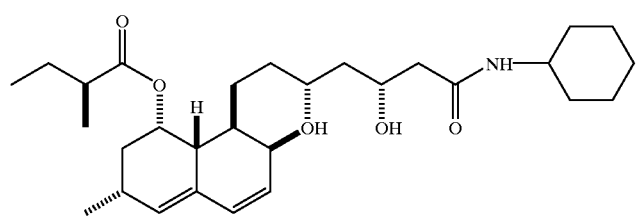

-continued

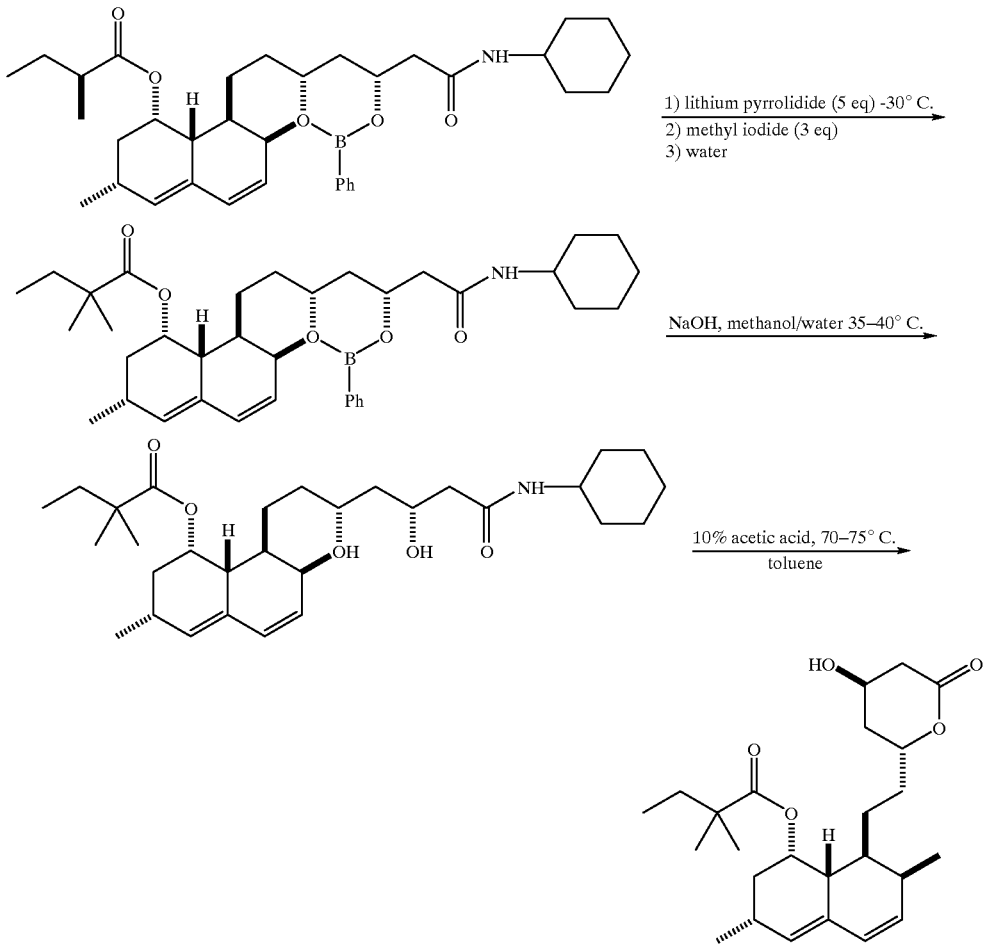

In U.S. Pat. No. 4,820,850 (89)/CA 1,287,063 (91, Merck), lovastatin is reacted with butylamine to produce lovastatin butylarnide. The two hydroxy groups in the butylamide are protected with tert-butyldimethylsilyl chloride to produce a disilylated lovastatin butylamide. The disilylated lovastatin butylamide is enolized with lithium pyrrolidide and the enolate is alkylated with methyl iodide to produce a disilylated simvastatin butylamide on aqueous workup. The silyl protecting groups are removed using hydrofluoric acid to produce simvastatin butylamide. The simvastatin butylamide is hydrolyzed using sodium hydroxide and, following acidification, the dihydroxy acid form of simvastatin is obtained. The dihydroxy acid compound is reacted with ammonium hydroxide to produce an ammonium salt which is then relactonized by heating to produce simvastatin.

Flowsheet for US 4,820,850 (89)/CA 1,287,063 (91)

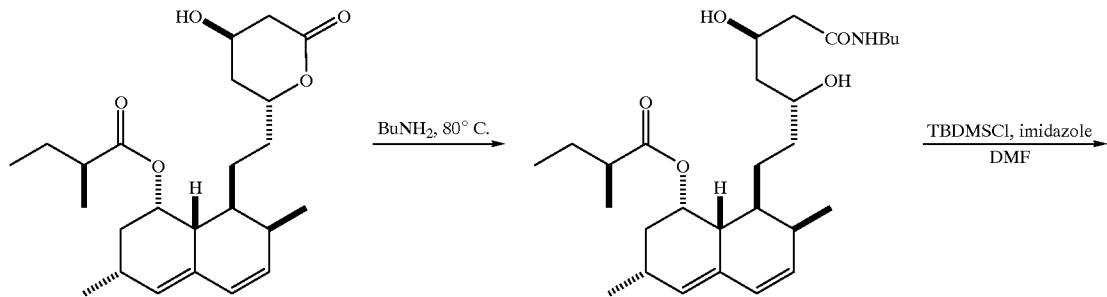

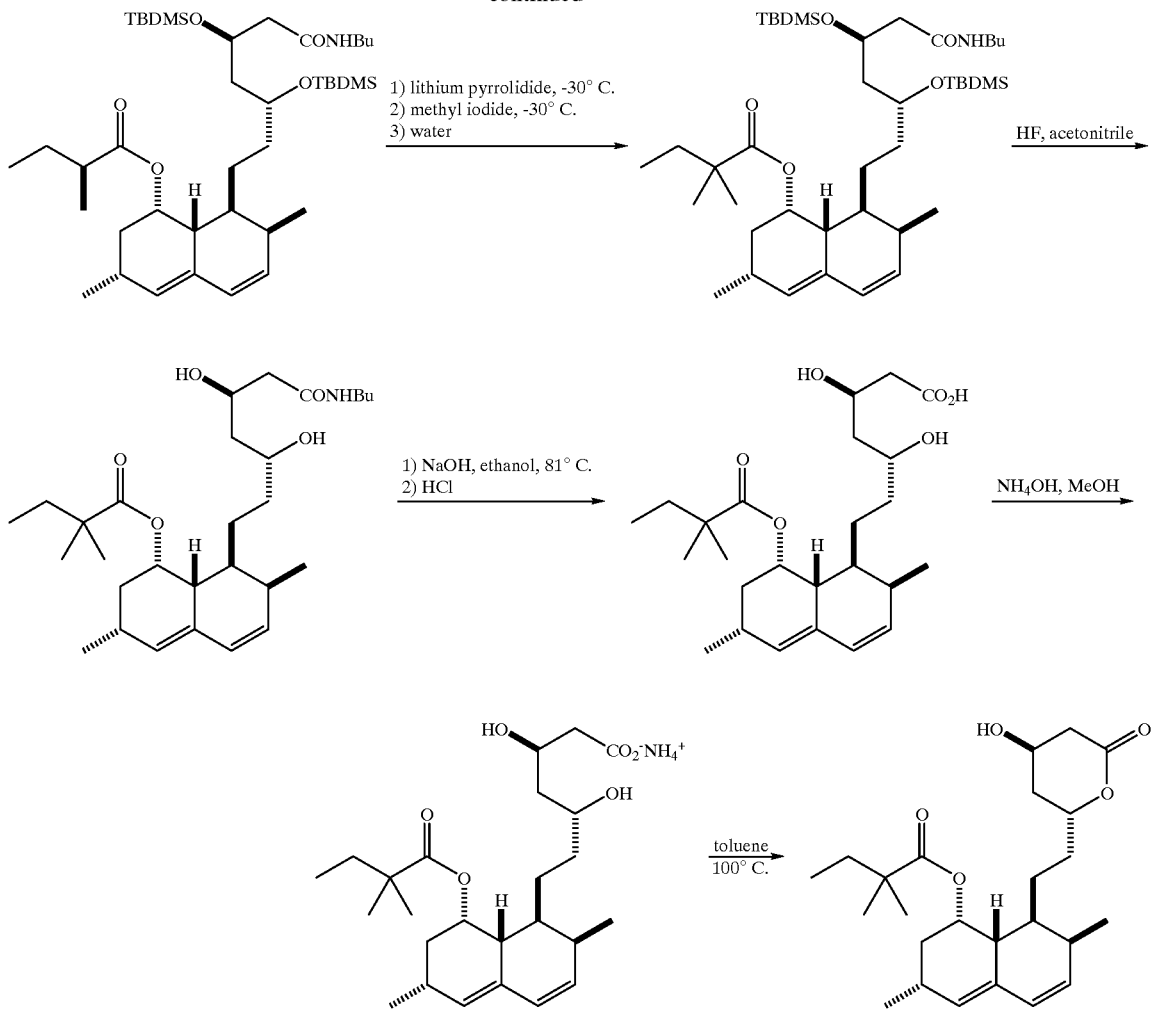

-continued

SUMMARY OF INVENTION

According to one aspect of the invention, simvastatin may be manufactured by reacting lovastatin with an organic boronic acid to produce a derivative of lovastatin with a boronate group thereafter methylating the 2-methylbutyryloxy group to form the 2,2-dimethylbutyryloxy group and thereafter removing the boronate group.

More broadly, according to another aspect of the invention, a compound containing a β-hydroxylactone group and also an aliphatic ester side- chain (with available α-hydrogens) may be reacted with an organic boronic acid. The boronate compound obtained therefrom may then be subjected to a subsequent enolate alkylation at the α-position of the aliphatic ester side chain. After the enolate alkylation of the compound, the boronate group may be removed and the alkylated compound may be recovered.

The present invention also relates to novel intermediates used for carrying out these processes and their use to manufacture the compounds including simvastatin. One such compound possesses the following general structural formula:

These processes all suffer from severe disadvantages such as excessive steps including those involved with the ring opening of the lactone group of lovastatin, the insertion and removal of protecting groups, and the necessity for relactonization.

It is therefore an object of this invention to provide a process (processes) for the manufacture of simvastatin which is more efficient requiring less steps than in the prior art processes without the problems associated therewith.

It is a further object of this invention to provide a process (processes) for the manufacture of compounds containing a β-hydroxy lactone group with available lactone α-hydrogens and also an aliphatic ester side-chain with available α-hydrogens wherein alkylation at the ester α-carbon requires less steps than in the prior art processes without the problems associated therewith.

Further and other objects of the invention will be realized by those skilled in the art from the following discussion of the invention, summary of invention and examples thereof.

DISCUSSION OF INVENTION

The present invention relates to the unexpected incorporation of a boronate group in lovastatin and results in deprotonation with high selectivity at the α-position of the 2-methylbutyrate side chain.

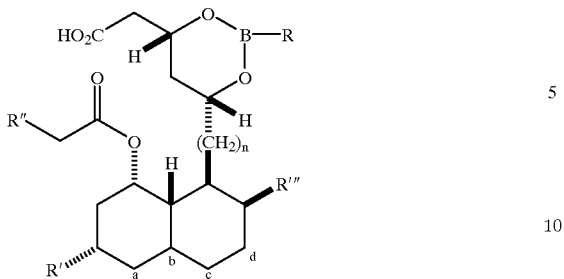

in which the bonds a-b and c-d are optionally single or double bonds; n=1 to 4; R is an alkyl group of 1–6 carbon atoms, a cycloalkyl group of 3–7 carbon atoms, or an aryl group optionally substituted by 1–4 substituents of halogen or lower alkyl in any combination; $R^I$ is selected from hydrogen, alkyl of 1–6 carbons, cycloalkyl of 3–7 carbon atoms, OH, $OR^{IV}$ ($R^{IV}$ is alkyl, cycloalkyl, aryl); $R^{II}$ is selected from hydrogen, alkyl of 1–6 carbons, cycloalkyl of 3–7 carbon atoms; $R^{III}$ selected from hydrogen, alkyl of 1–6 carbons, cycloalkyl of 3–7 carbon atoms.

The present invention thus relates to a novel unexpected process for the production of simvastatin from lovastatin, processes for the preparation of the intermediates used therein, and the novel intermediates themselves.

The invention also relates to a process for the purification of lovastatin through the formation of novel crystalline compounds (II).

According to one aspect of the present invention a process of the invention may be carried out as follows:

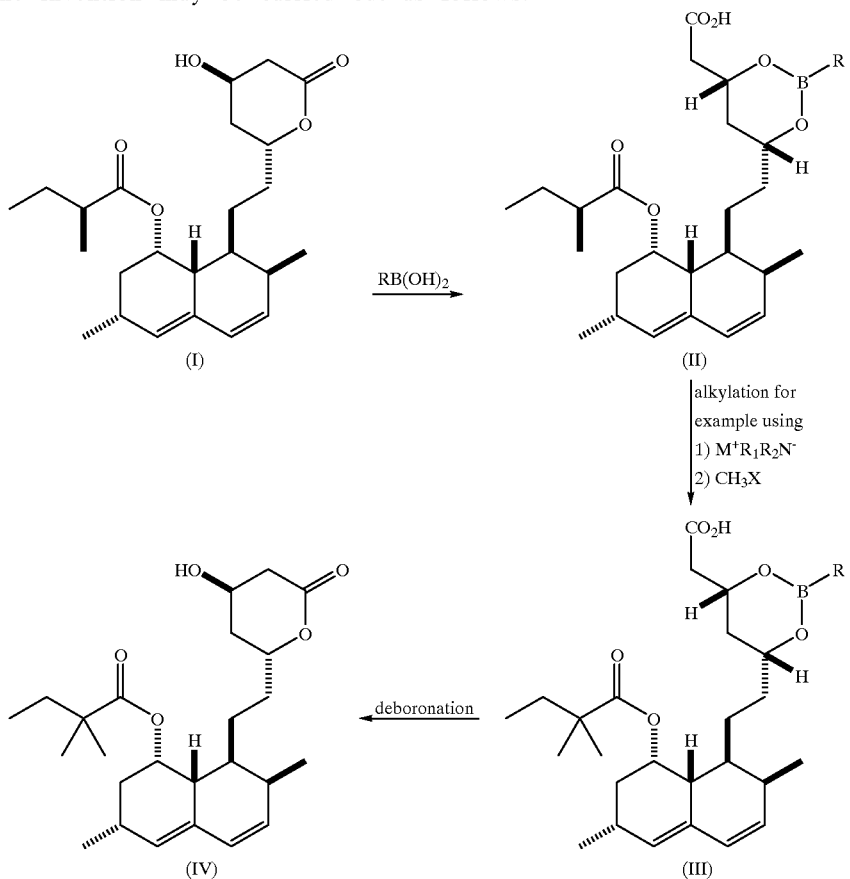

wherein R may be selected from an alkyl group of 1–6 carbon atoms, a cycloalkyl group of 3–7 carbon atoms, substituted or unsubstituted, or an aryl group optionally substituted by 1–4 substituents of halogen or lower alkyl in any combination, $R_1$ and $R_2$ are selected from methyl, isopropyl, trimethylsilyl, cyclohexyl, and cyclo-$(CH_2)_4$, M is selected from lithium, sodium, and potassium, and X is selected from chlorine, bromine, and iodine.

Generally to make simvastatin, lovastatin (I) is heated together with an equimolar amount of an aryl or alkylboronic acid, preferably phenylboronic acid, in a nonpolar solvent, preferably toluene, from which water may optionally be azeotropically removed and the lovastatin boronate (II) which is formed is isolated by concentration of the reaction mixture and crystallization with a suitable cosolvent, preferably hexanes.

The crystalline nature of (II) allows for a method of purification of lovastatin which is used in the process and thereby provides a significant advantage over previous prior art.

Thus by recovering lovastatin boronate and removing the boronate to make lovastatin in a similar manner as the removal of the boronate from the simvastatin boronate (III) as persons skilled in the art would understand, lovastatin can be purified.

According to another aspect of the invention, lovastatin may be agitated in the presence of a dehydrating agent, preferably molecular sieves, in an organic solvent, preferably tetrahydrofuran, at ambient temperatures and the lovastatin boronate which is produced may be isolated by filtration and evaporation.

Lovastatin boronate (II) is treated in one embodiment at low temperatures, between –30° C. and –60° C., preferably –55° C., in an ether solvent, preferably tetrahydrofuran, with an alkali metal salt (selected from lithium, sodium, and potassium) of a secondary amine selected from dimethylamine, pyrrolidine, dicyclohexylamine, 1,1,1,3,3,3-hexamethyldisilazane, and diisopropylamine, preferably pyrrolidine, to produce an alkali metal enolate intermediate. The enolate intermediate is methylated with a suitable methyl halide, preferably methyl iodide, at temperatures between –10° C. and –30° C. to produce a simvastatin boronate (III). The reaction product is isolated by an acidic workup and concentration.

Simvastatin boronate (III) is heated in the presence of a suitable diol solvent selected from ethylene glycol, 1,3-propanediol, or neopentyl glycol, under thermal conditions. The product is isolated by concentration of the reaction mixture, dilution with water, and extraction with an organic solvent. The organic solvent is concentrated to a minimum volume and simvastatin is isolated by the addition of a cosolvent and filtration.

Alternatively, III may be agitated in a mixture of water and an organic solvent, preferably methanol, under high dilution conditions to produce simvastatin in its acid form. Simvastatin acid may be isolated by extraction or crystallization and relactonized to produce simvastatin.

Alternatively, III may be dissolved in an organic solvent and recirculated over a supported diol or polyol stationary phase to which the boronate moiety of III becomes attached. The organic solution is concentrated to obtain simvastatin.

Simvastatin may also be produced from III by reacting III with a stoichiometric amount of a diol selected from ethylene glycol, 1,3-propanediol, neopentyl glycol or various carbohydrate diols in an organic solvent or organic solvent/water combination under thermal conditions. The resulting solution of simvastatin is extracted with a second immiscible organic solvent to remove the cyclic boronate byproduct. Simvastatin is isolated by concentration, the addition of a suitable cosolvent to effect crystallization, and filtration.

The crude simvastatin obtained by the methods described above may be brought to pharmaceutically acceptable levels by recrystallization from suitable solvents or combinations of solvents.

EXAMPLES

Example 1

Preparation of Lovastatin Phenylboronate

A suspension of lovastatin (350 g, 0.865 mmol), phenylboronic acid (110.8 g, 0.909 mmol) and toluene (1.75 L) was heated with agitation under a nitrogen atmosphere. A reflux temperature of 100–105° C. was maintained for 55 minutes as water was collected and separated from the reaction mixture. The solution was cooled and 1.39 L of toluene was removed by vacuum distillation at 40–50° C. The concentrated solution was treated with hexanes (3.15 L) between 40–50° C. The resulting suspension was cooled to 0–5° C. for 2 hours and the product was filtered and washed with 0–5° C. hexanes (350 mL). The product was dried at 35–40° C. under vacuum to provide 427.9 g (37%) of lovastatin phenylboronate at >99% purity by HPLC.

Example 2

Alkylation of Lovastatin Phenylboronate Using Lithium Pyrrolidide

A 2L 3-necked flask was charged with pyrrolidine (56 mL, 0.67 mol) and dry THF (453 g) under a nitrogen atmosphere. n-Butyllithium (419 mL, 1.6 M hexane solution, 0.67 mol) was added dropwise at a temperature between –20 and –25° C. over a period of 1 hour. The solution was maintained at this temperature for 30 minutes and then cooled to –55 to –60° C. A solution of lovastatin phenylboronate (101.7 g, 0.20 mol) in 274.7 g of THF was cooled to a temperature of –50° C. and then added to the cold lithium pyrrolidide solution at a rate such that the internal temperature was between –50 and –55° C. during the addition. The reaction was held at this temperature for 4 hours and then methyl iodide (116.4 g, 0.82 mol) was added at a temperature below –55°C. The reaction was stirred for 13 hours at –15 to –20° C. and then quenched with 500 mL of 2M HCl at a temperature below 0° C. After warming to 20° C., the layers were separated and the aqueuous layer was extracted with ethyl acetate. The combined organic layers were washed with 5% $NaHSO_3$ solution and deionized water. The solution was filtered through a Celite pad and concentrated to yield 102.8 g (98.4%) of crude simvastatin phenylboronate at >95% purity by HPLC. A portion of the above material (50.0 g) was charged into a nitrogen purged flask with acetonitrile (100 mL). The suspension was heated at 110° C. for 3 hours and then cooled to –5 to –10° C. for 1 hour. The product was filtered and washed with 25 mL of –5° C. acetonitrile and dried under vacuum to provide 43.7 g of simvastatin phenylboronate at >99% purity by HPLC.

Example 3

Alkylation of Lovastatin Methylboronate Using Lithium Pyrrolidide

According to the method described in Example 2, from 8.9 g of lovastatin methylboronate there was obtained simvastatin methylboronate of >90% purity in 96% yield.

Example 4

Alkylation of Lovastatin Phenylboronate Using Lithium Dimethylamide

According to the method described in example 2, from 10.2 g of lovastatin phenylboronate and substituting lithium dimethylamide for lithium pyrrolidide, there was obtained 75% of simvastatin phenylboronate of >95% purity.

Example 5

Preparation of Simvastatin from Simvastatin Phenylboronate Using 1,3-Propanediol A suspension of simvastatin phenylboronate (30.0 g) and 1,3-propanediol (450 mL) was heated at 105 to 107° C. at 0.2 mm Hg. After 1 hour, 182 mL of distillate was collected and the reaction was cooled to 20 to 25° C. Deionized water (270 mL) was added and toluene (3×75 mL) was used to extract the mixture. The combined toluene layers were washed with water (2×30 mL). The organic solution was heated at reflux for 1 hour and water was azeotropically removed. The solution was concentrated to a final volume of 24 mL under vacuum at 48 to 50° C. To the concentrated solution was added hexanes (215 mL) over 10 minutes. The resulting slurry was cooled to 0 to 5° C. and filtered. The crude simvastatin was washed with 0 to 5° C. hexanes and dried under vacuum to yield 21.0 g (88%) of simvastatin.

Example 6

Preparation of Simvastatin from Simvastatin Phenylboronate Using Neopentyl Glycol A mixture of simvastatin phenylboronate (5.22 g, 0.010 mol), toluene (31 mL), and neopentyl glycol (1.11 g, 0.0107 mol) was heated under a nitrogen atmosphere at 77 to 79° C. for 1 hour and 40 minutes. The solution was concentrated under reduced pressure at a bath temperature of 60° C. to a final volume of 5 mL and n-heptane (160 mL) was added at a temperature of 50–60° C. The crude simvastatin was filtered and washed with heptane to provide 3.17 g (76%) of simvastatin. By appropriate manipulation of the conditions and reagents, compounds such as the compactin analogue of simvastatin may be prepared.

As many changes can be made to the invention without departing from the scope thereof, it is intended that all material contained in the embodiments be interpreted as illustrative of the invention and not in a limiting sense.

What is claimed is:

1. A process for the preparation of a compound of formula (II)

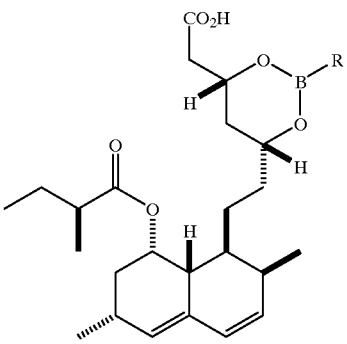

by reacting a compound of formula (I)

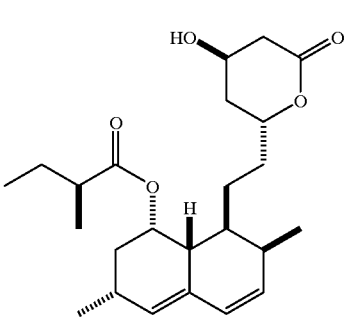

with an alkyl, cycloalkyl, or arylboronic acid in a non-polar solvent.

2. A process for the purification of lovastatin by a process wherein the compound of formula II

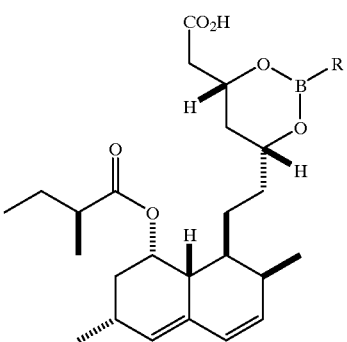

is recovered from solution by filtration, the boronate group is removed from compound of formula (II) by reacting the compound of formula (II) with a hydroxylic reagent and recovering the resulting lovastatin by crystallization.

3. The process of claim 1 further comprising reacting a compound of formula (II)

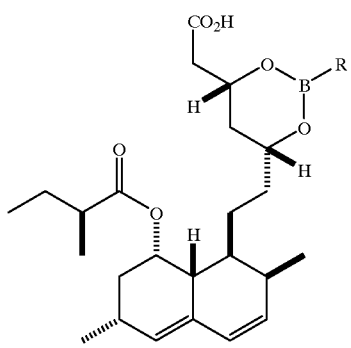

(II)

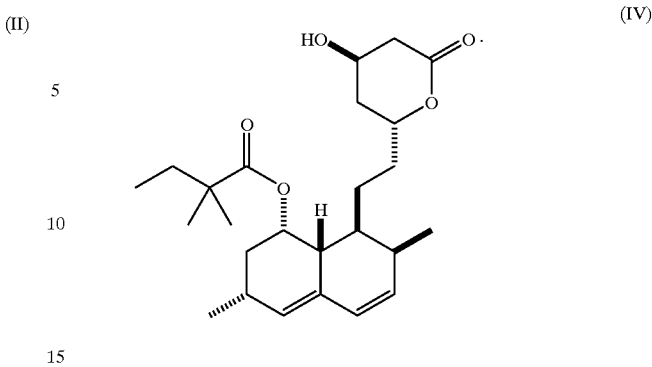

5. The process of claim 4 wherein the reaction of a compound of formula (III)

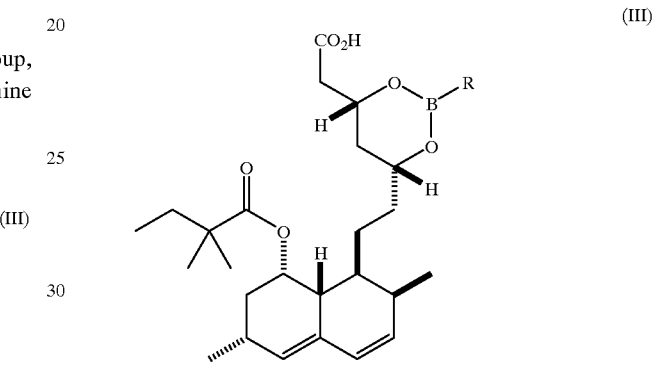

(III)

with a methyl halide, CH₃X, in which X is a leaving group, in the presence of an alkali metal salt of a secondary amine to produce a compound of formula (III)

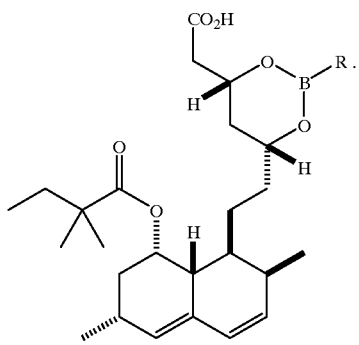

(III)

with the diol or polyol reagent is selected from the group of processes comprising one of the following processes:

(i) heating (III) with the diol or polyol as solvent,
(ii) heating (III) with a stoichiometric amount of diol or polyol in an organic solvent,
(iii) diluting (III) in a mixture of water and organic solvent, or
(iv) circulating a solution of (III) over a supported diol or polyol stationary phase.

6. A compound of formula (II)

4. The process of claim 3 further comprising reacting a compound of formula (III)

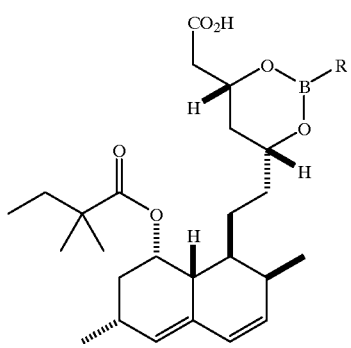

(III)

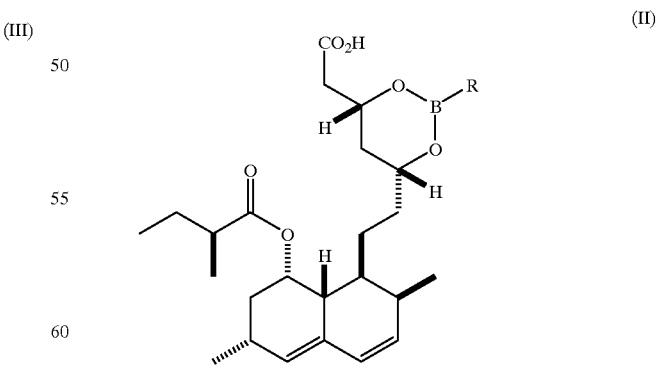

(II)

with a diol or a polyol reagent to produce a compound of formula (IV)

where R is selected from alkyl of 1–6 carbons, cycloalkyl of 3–7 carbons, substituted or unsubstituted, or aryl optionally substituted by 1–4 substituents of halogen or lower alkyl in any combination.

7. A compound of formula (III)

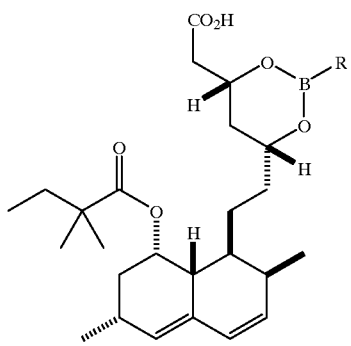
(III)

where R is selected from alkyl of 1–6 carbons, cycloalkyl of 3–7 carbons, substituted or unsubstituted, or aryl optionally substituted by 1–4 substituents of halogen or lower alkyl in any combination.

8. A process for manufacturing simvastatin comprising reacting lovastatin (I)

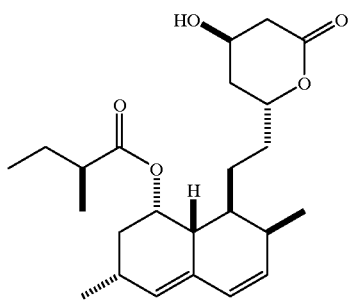
(I)

with an organic boronic acid $RB(OH)_2$ to produce a derivative of lovastatin (II)

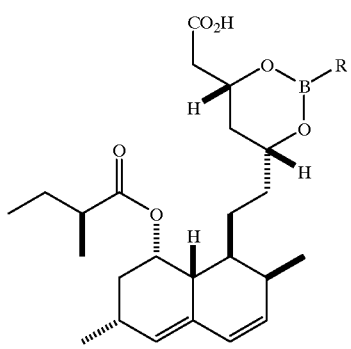
(II)

with a boronate group attached to the C-4 carbon of the pyranyl group, methylating the 2-methylbutyryloxy group of (II)

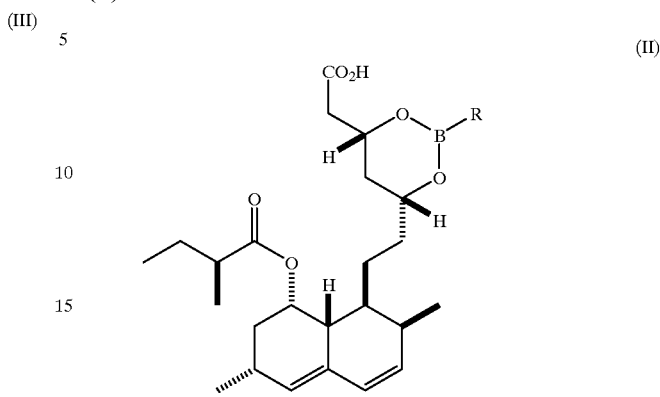
(II)

to form the 2,2-dimethylbutyryloxy group of (III)

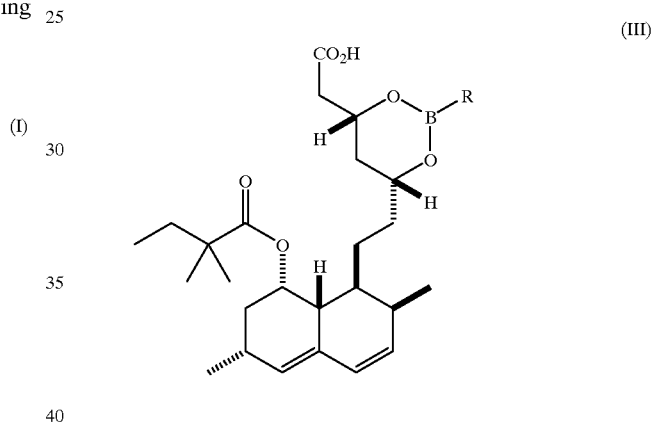
(III)

and thereafter removing the boronate group to produce simvastatin (IV)

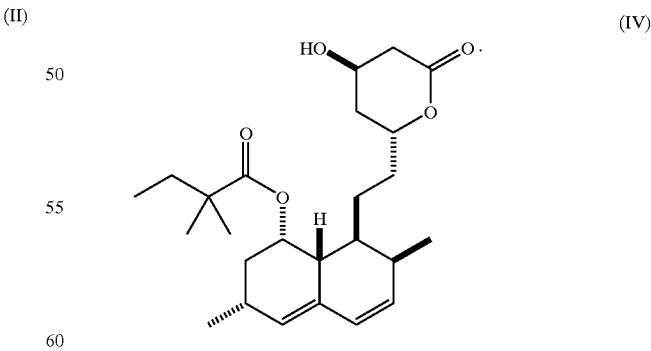
(IV)

9. The process for the manufacture of simvastatin by the following steps:

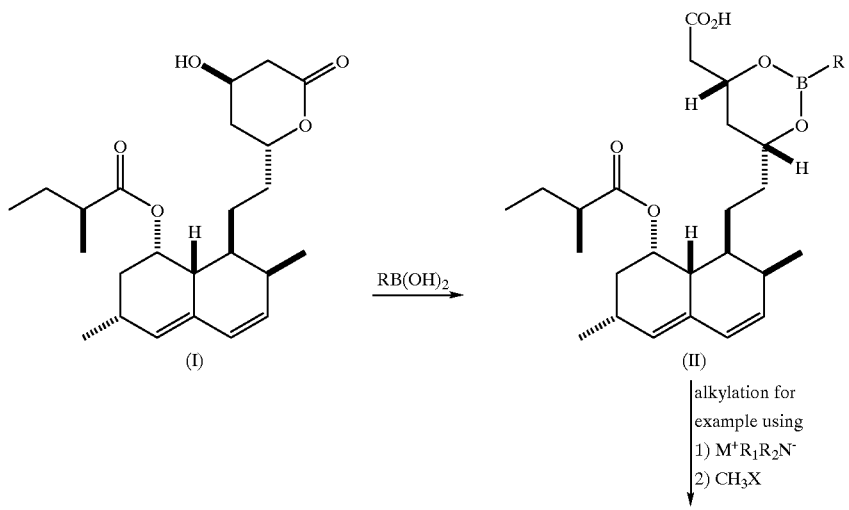
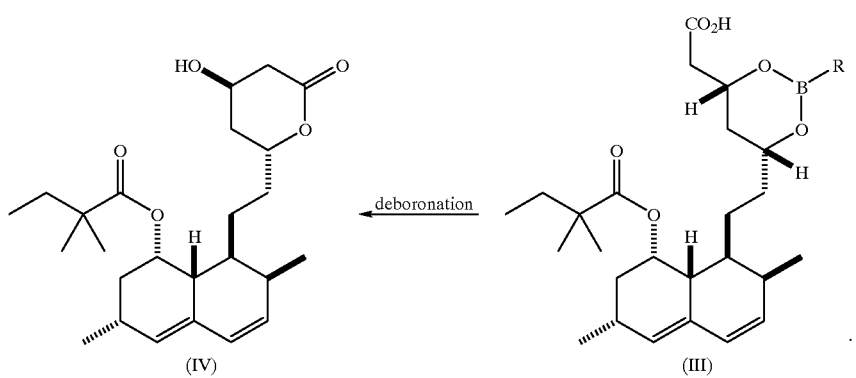
10. The process of claim 8 or 9 further comprising the step of recovering simvastatin.
11. The process of producing compound (III) from compound (II)
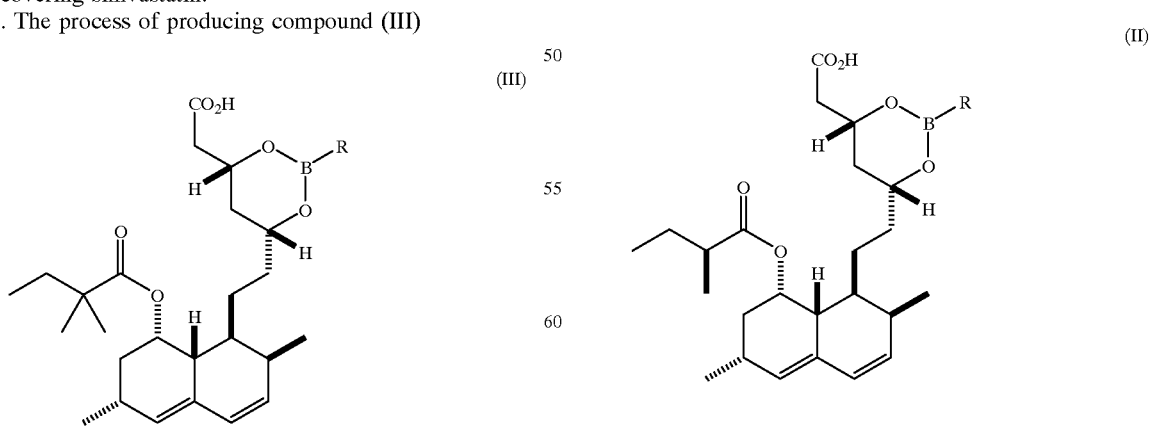

by metallation of compound (II)

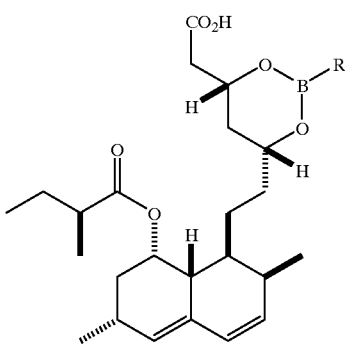

(II)

using an alkalai metal salt of a secondary amine to generate an enolate and thereafter methylating the resultant intermediate by reacting with a methylating agent.

12. The process of claim 11 wherein the methylation comprises reacting (II) in the presence of (1) $M^+R_1R_2N^{3-1}$ where M is selected from lithium, sodium and potassium and $R_1,R_2$ are selected from: $R_1=R_2=$methyl; $R_1=R_2=$isopropyl; $R_1=R_2=$cyclohexyl; $R_1=R_2=(CH_3)_3$ Si; $R_1+R_2=$cyclo-$(CH_2)_4$ and (2) $CH_3$ X wherein X is selected from chlorine, bromine, and iodine.

13. The process of claim 12 further comprising producing simvastatin by removing the boronate group from the compound of formula (III)

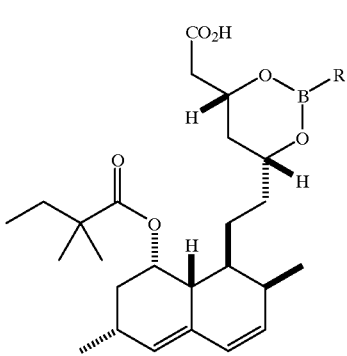

(III)

and thereafter recovering simvastatin.

14. A process of boronating a compound containing a β-hydroxylactone group with available lactone α-hydrogens and also an aliphatic ester side-chain with available α-hydrogens, the process comprising reacting such compound with an organic boronic acid of the formula RB(OH)$_2$.

15. The process of claim 14 wherein the resultant product of claim 14 is subjected to an enolate alkylation reaction at the α-position of the otherwise normally less-acidic aliphatic ester side-chain.

16. The process of claim 15 further comprising deboronating the compound of claim 15.

17. The process of claim 16 further comprising recovering the compound of claim 16.

18. The process of claims 8, 9, 10, 11, 12, 13, 14, 15, 16 or 17 wherein the R group is alkyl, cycloalkyl, or aryl wherein the alkyl group contains from 1–6 carbon atoms, the cycloalkyl group contains from 3–7 carbon atoms, and the aryl group is optionally substituted by 1–4 substituents of halogen or lower alkyl in any combination.

19. The process of claim 15 wherein the enolate alkylation is methylation and wherein the methylation comprises reacting (II)

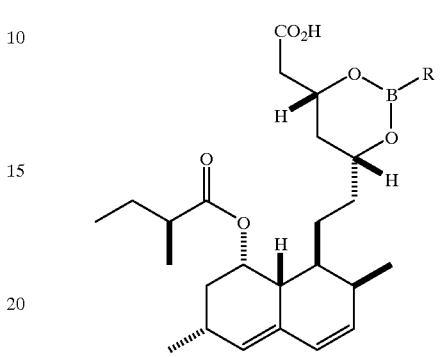

(II)

in the presence of (1) $M^+R_1R_2N^{3-1}$ where M is selected from lithium, sodium and potassium and $R_1,R_2$ are selected from: $R_1=R_2=$-methyl; $R_1=R_2=$isopropyl; $R_1=R_2=$cyclohexyl; $R_1=R_2=(CH_3)_3$ Si; $R_1+R_2=$cyclo-$(CH_2)_4$ and (2) $CH_3X$ wherein X is selected from chlorine, bromine, and iodine.

20. The compound of the following structural formula:

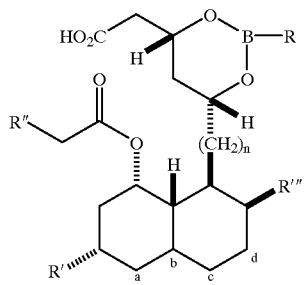

in which the bonds a-b and c-d are optionally single or double bonds; n=1 to 4; R is an alkyl group of 1–6 carbon atoms, a cycloalkyl group of 3–7 carbon atoms, or an aryl group optionally substituted by 1–4 substituents of halogen or lower alkyl in any combination; $R^I$ is selected from hydrogen, alkyl of 1–6 carbons, cycloalkyl of 3–7 carbon atoms, OH, $OR^{IV}$ wherein ($R^{IV}$ is alkyl, cycloalkyl, aryl); $R^{II}$ is selected from hydrogen, alkyl of 1–6 carbons, cycloalkyl of 3–7 carbon atoms; $R^{III}$ is selected from hydrogen, alkyl of 1–6 carbons, cycloalkyl of 3–7 carbon atoms.

21. The process of claim 9 wherein the boronate group emanates from the compound RB(OH)$_2$ wherein the R is selected from substituted and unsubstituted aryl and alkyl groups.

22. The process of claim 21 wherein R is unsubstituted phenyl.

23. The process of claim 9 or 22 wherein the boronate is removed using a diol or a polyol.

24. The process of producing simvastatin as follows:

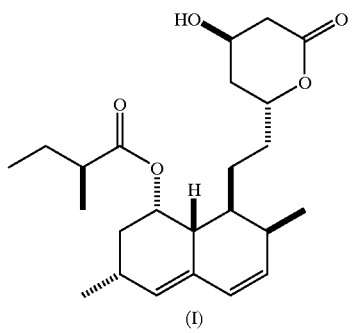

(I)

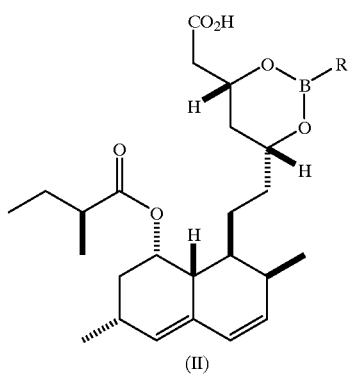

(II)

insertion of boronate group (using RB(OH)$_2$) where R is selected from substitute and unsubstituted alkyl and aryl groups)

methylating the 2-methyl-butyryloxy group to form the 2,2-dimethylbutyryloxy group by using
1) $M^+R_1R_2N^-$
2) $CH_3X$
where M is selected from Na, Li, K, R$_1$ and R$_2$ are selected from methyl, cyclohexyl, trimethylsilyl, isopropyl, and cyclo-(CH$_2$)$_4$, and X is selected from Cl, Br, and I

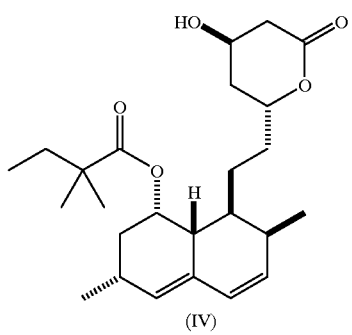

(IV)

removal of boronate group by using a diol or polyol

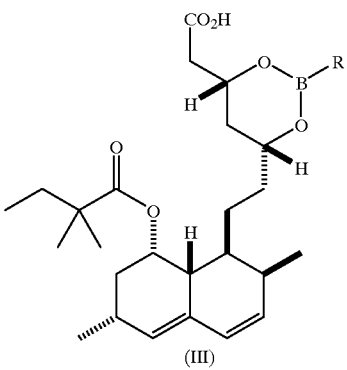

(III)

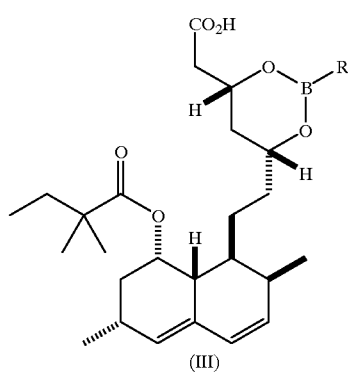

(III)

to produce

-continued
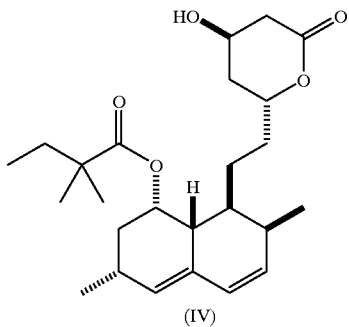
(IV)
25. The process of producing:
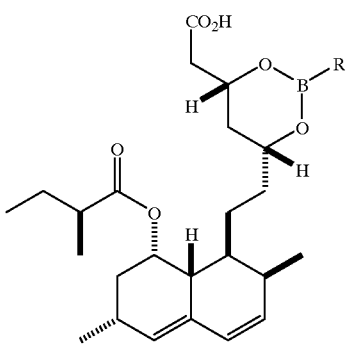
(II)
by insertion of a boronate group into
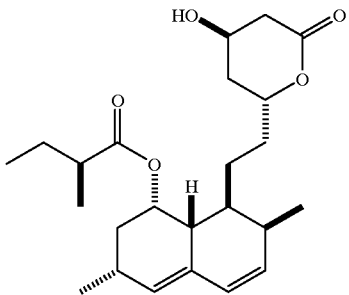
(I)
with an alkyl, cycloalkyl or aryl boronic acid in a non-polar solvent.
26. The process of methylating the 2-methylbutyryloxy group of compound II
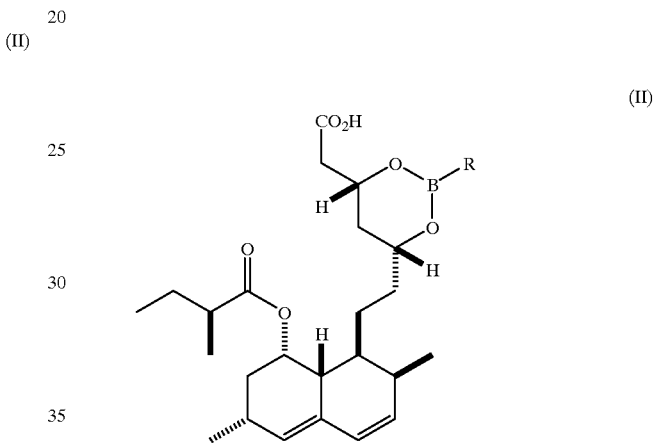
(II)
to produce
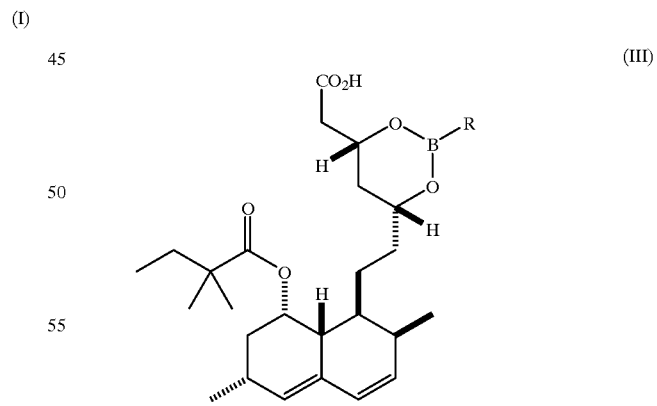
(III)

wherein compound (II)

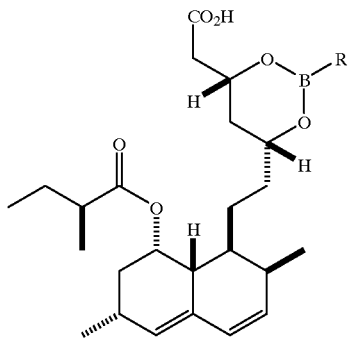
(II)

is reacted with an alkalai metal salt of a secondary amine and thereafter methylating the intermediate compound so produced by reacting it with a methylating agent to produce the compound of formula (III)

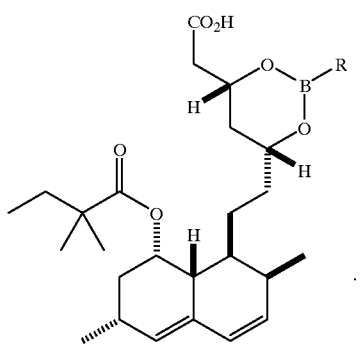
(III)

27. The process of deboronating

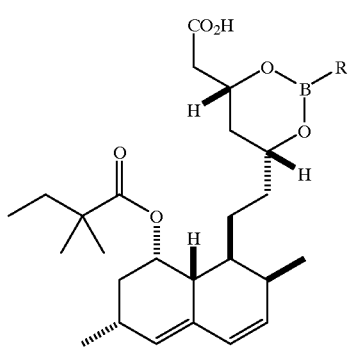
(III)

to produce

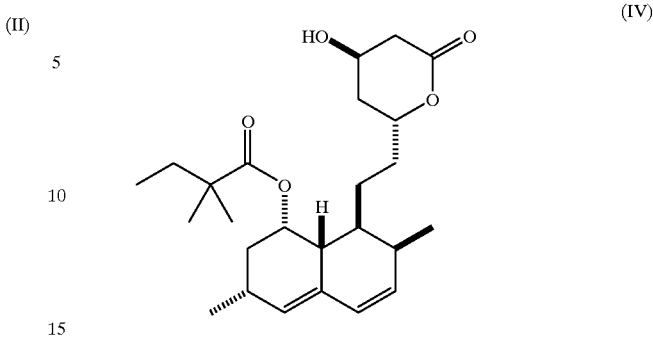
(IV)

by reacting the compound of formula (III)

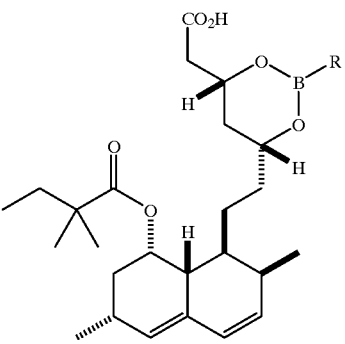
(III)

with a hydroxylic compound to produce the compound of formula (IV)

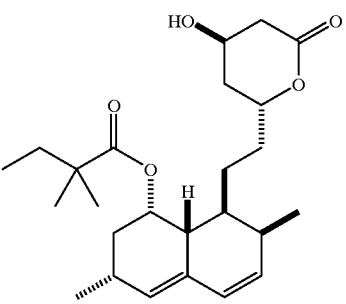
(IV)

28. The process of claim 25 wherein the boronate group emanates from the compound $RB(OH)_2$ wherein R is selected from substituted and unsubstituted aryl and alkyl groups.

29. The process of claim 28 wherein R is unsubstituted phenyl.

30. The process of clain 27 wherein the boronate is removed by using a diol or polyol.

31. The process of claim 1 wherein water has been removed azeotopically from the non-polar solvent.

32. The process of claim 1 or 31 wherein the non-polar solvent is toluene.

33. The process of claim 2 wherein the hydroxylic reagent is selected from the group consisting of diols and polyols and mixtures thereof.

34. The process of claim 11 wherein the methylating agent is a methyl halide.

35. The process of claim 25 wherein water has been removed azeotopically from the non-polar solvent.

36. The process of claim 25 or 35 wherein the non-polar solvent is toluene.

37. The process of claim 26 wherein the methylating agent is a methyl halide.

38. A process for manufacturing simvastatin comprising reacting lovastatin (I) with an organic boronic acid RB(OH)$_2$ to produce a derivative of lovastatin (II) with a boronate group, methylating the 2-methylbutyryloxy group of (II) to form the 2,2-dimethylbutyryloxy group of (III) and thereafter removing the boronate group to produce simvastatin (IV) wherein R may be selected from an alkyl group of 1–6 carbons, cycloalkyl of 3–7 carbons, substituted or unsubstituted, or aryl optionally substituted by 1–4 substituents of halogen or lower alkyl or combinations thereof.

39. The process of claim 38 in which R is phenyl.

40. The process of claim 38 in which R is methyl.

41. A process of boronating a compound containing a β-hydroxylactone group and also an aliphatic ester side-chain (with available α-hydrogens), the process comprising reacting such compound with an organic boronic acid of the formula RB(OH)$_2$, wherein R may be selected from an alkyl group of 1–6 carbons, cycloalkyl of 3–7 carbons, substituted or unsubstituted, or aryl optionally substituted by 1–4 substituents of halogen or lower alkyl or combinations thereof.

42. The process of claim 41 wherein the resultant product of claim 4 is subjected to an enolate alkylation reaction at the α-position of the aliphatic ester side-chain.

43. The process of claim 42 further comprising deboronating the compound produced by the process of claim 42.

44. The process of claim 43 further comprising recovering the compound produced by the process of claim 43.

45. The process of claims 42, 43 or 44 wherein the R group is alkyl, cycloalkyl, or aryl wherein the alkyl group contains from 1–6 carbon atoms, the cycloalkyl group contains from 3–7 carbon atomns, and the aryl group is optionally substituted by 1–4 substituents of halogen or lower alkyl or combinations thereof.

* * * * *